(12) United States Patent
Hagemeyer et al.

(10) Patent No.: US 6,603,038 B1
(45) Date of Patent: Aug. 5, 2003

(54) METHOD FOR PRODUCING CATALYSTS CONTAINING METAL NANOPARTICLES ON A POROUS SUPPORT, ESPECIALLY FOR GAS PHASE OXIDATION OF ETHYLENE AND ACETIC ACID TO FORM VINYL ACETATE

(75) Inventors: Alfred Hagemeyer, Frankfurt (DE); Uwe Dingerdissen, Seeheim-Jugenheim (DE); Klaus Kuhlein, Kelkheim (DE); Andreas Manz, Sinzheim (DE); Roland Fischer, Neckargemund (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 09/485,804
(22) PCT Filed: Aug. 1, 1998
(86) PCT No.: PCT/EP98/04819

§ 371 (c)(1),
(2), (4) Date: Apr. 28, 2000

(87) PCT Pub. No.: WO99/08791
PCT Pub. Date: Feb. 25, 1999

(30) Foreign Application Priority Data

Aug. 13, 1997 (DE) ......................................... 197 34 974

(51) Int. Cl.[7] ............................. B01J 23/00; B01J 23/02; C07C 27/10
(52) U.S. Cl. ................... 560/241.1; 502/325; 502/330
(58) Field of Search ................. 502/325, 330; 560/241.1

(56) References Cited

FOREIGN PATENT DOCUMENTS

| GB | 2006261 | 5/1979 |
| WO | 9408714 | 10/1993 |
| WO | 9736678 | 3/1997 |

*Primary Examiner*—Paul J. Killos
(74) *Attorney, Agent, or Firm*—Muserlian, Lucas and Mercanti

(57) ABSTRACT

The invention relates to a method for producing a catalyst containing one or several metals from the group of metals comprising the sub-groups Ib and VIIIb of the periodic table on porous support particles, characterized by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

27 Claims, No Drawings

METHOD FOR PRODUCING CATALYSTS CONTAINING METAL NANOPARTICLES ON A POROUS SUPPORT, ESPECIALLY FOR GAS PHASE OXIDATION OF ETHYLENE AND ACETIC ACID TO FORM VINYL ACETATE

This application is a 371 of PCT/EP98/04819 filed Aug. 1, 1998.

Process for producing catalysts comprising nanosize metal particles on a porous support, in particular for the gas-phase oxidation of ethylene and acetic acid to give vinyl acetate.

DESCRIPTION

The invention relates to a process for producing a catalyst comprising one or more metals selected from the group of metals encompassing transition groups Ib and VIIIb of the Periodic Table of the Elements on porous support particles. Here, the metals are present as nanosize particles in the finished catalyst. In particular, the invention relates to the production of "coated" catalysts on porous, preferably nanoporous, supports by this method.

Catalysts, preferably coated catalysts, can be used for many heterogeneously catalyzed reactions such as hydrogenations and oxidations. Among other things, Pd/Au coated catalysts are extremely well suited to the catalysis of the gas-phase oxidation of ethylene and acetic acid to give vinyl acetate. Here, the catalytically active metals are deposited in the form of a shell on or in the outermost layer of the support. They are often produced by penetration of the support with metal salts into a surface region and subsequent precipitation by alkalis to form water-insoluble Pd/Au compounds.

GB-A-1 283 737 discloses the production of a coated noble metal catalyst by preimpregnation of the support with an alkaline solution and saturation with 25–90% water or alcohol. Subsequent impregnation with Pd salts and reduction of the precipitated salts to the metal gives coated catalysts in which the penetration depth of the noble metal is said to be up to 50% of the pellet radius.

According to U.S. Pat. No. 3,775,342 and U.S. Pat. No. 3,822,308, coated catalysts are produced by impregnating the support with a solution of Pd/Au salts and with an aqueous base, preferably NaOH, which results in precipitation of insoluble palladium hydroxide and gold hydroxide in a shell-like surface zone of the pellets. The hydroxides which have been fixed in the shell in this way are then reduced to the metals.

GB-A-1 521 652 obtains coated catalysts of the egg white type, i.e. only an inner ring of the spherical $SiO_2$ support contains the noble metals while the inner core and a thin outer shell remain virtually free of noble metal, by a comparable procedure (preimpregnation with Pd, Au salts, drying, base precipitation, reduction).

U.S. Pat. No. 4,048,096 teaches the precipitation of water-insoluble Pd and Au compounds on the support preimpregnated with Pd/Au salts using sodium silicates in place of NaOH. The thickness of the shell is less than 0.5 mm.

U.S. Pat. No. 5,567,839 precipitates water-insoluble Pd and Au compounds on the support preimpregnated with Pd/Au salts using barium hydroxide in place of NaOH. The thickness of the shell is 1 mm. The catalyst can also be doped with barium acetate.

EP-A-0 519 435 discloses the production of a Pd/Au/K or Pd/Cd/K coated catalyst in which a specific support material is washed with an acid prior to impregnation and is treated with a base after impregnation.

U.S. Pat. No. 5,314,858 concerns double fixing of the noble metals in an outer shell by means of two separate precipitation steps using NaOH.

WO-A-94/08714 achieves particularly uniform shells by rotational motion of the support impregnated with Pd, Au salts during the fixing step, i.e. immersed in the alkaline fixing solution (NaOH).

EP-A-0 723 810 employs pretreatment (impregnation) of the support with metal salt solutions to produce a support which is preferably doped with Al, Zr, Ti and is subsequently used for the above-described base precipitation to form a Pd/Au/K coated catalyst.

U.S. Pat. No. 5,347,046 describes the use of Cu, Ni, Co, Fe, Mn, Pb, Ag as promoters in Pd/Au systems on $SiO_2$ supports pretreated with alkali metal hydroxide and alkali metal silicate.

Another method of producing coated catalysts is prenucleation with metals and subsequent deposition of the intended amount of noble metals.

The published Japanese patent application 48-10135/1973 describes the production of a Pd/Au coated catalyst. Here, a small amount of reduced metal (gold) is deposited on the porous support in a pretreatment step. Subsequent impregnation results in deposition of Pd in a surface zone having a thickness of about 15% of the particle radius.

U.S. Pat. No. 4,087,622 teaches the production of coated catalysts by prenucleation with (reduced) Pd/Au metal nuclei in a low concentration, by impregnating the porous $SiO_2$ or $Al_2O_3$ support with a Pd/Au salt solution, drying it and then reducing the Pd/Au salt to the metal. This prenucleation step is followed by deposition of the catalytically necessary amount of noble metal, i.e. the main amount which is then concentrated in a shell near the surface.

The use of different variants of "deficiency techniques" likewise enables coated catalysts to be obtained.

These include, inter alia:
- deficiency of precipitants, e.g. NaOH, in combination with multiple precipitation;
- deficiency of impregnation solution (less than the pore volume of the support);
- limitation of the contact time during absorption of the noble metals;
- insufficient noble metal concentration (per impregnation step) combined with multiple impregnation; and
- combinations of the abovementioned variants.

EP-A-0 565 952 describes the formation of shell-like Pd/K/Au, Pd/K/Ba and Pd/K/Cd catalysts by atomizing a solution of appropriate metal salts by means of ultrasound and then applying this to the support particles in such a limited a mount and within such a restricted time and commencing drying in such a way that the catalytically active metal salts cannot penetrate to the core of the support particles, but only into an outer part of varying thickness, namely the shell.

According to EP-A-0 634 214, coated catalysts are obtained by spraying a viscous solution of appropriate metal salts in the form of droplets or liquid jets onto the support particles, where the solution volume in each spraying step is 5–80% of the pore volume of the support particles and drying is commenced immediately after spraying.

EP-A-0 634 209 obtains coated catalysts by impregnating the support particles with a viscous solution of appropriate metal salts, where the solution volume in each impregnation step is 5–80% of the pore volume of the support particles and drying is commenced immediately after each impregnation step.

According to EP-A-0 634 208, coated catalysts are obtained by impregnating the support particles with a viscous solution of salts of the appropriate elements and then drying them, where the solution volume in the impregnation is more than 80% of the pore volume of the support particles and the duration of impregnation and the time to commencement of drying are made so short that the metal salts specified are present in a shell of 5–80% of the pore volume of the support particles after the end of drying.

U.S. Pat. No. 5,576,457 concerns Pd/Cd/K coated catalysts which are doped with Zr and/or Re, where the shell can be produced as described in EP 0634208, EP 0634209 or EP 0634214.

U.S. Pat. No. 5,591,688 describes fluidized-bed VAM catalysts (VAM=vinyl acetate (monomer)) comprising Pd—Ba, Au, La, Nb, Ce, Zn, Pb, Ca, Sr, Sb on silica, alumina or zirconia, using halide-free precursors.

U.S. Pat. No. 5,536,693 describes fluidized-bed VAM catalysts comprising Pd—Au, Cd, Bi, Cu. Mn, Fe, Co, Ce, U which are produced by milling a fixed-bed catalyst precursor preimpregnated with Pd—M and compounding with a binder comprising silica, alumina, zirconia or titania.

The production and stabilization of nanosize noble metal particles in solution is prior art. Other customary terms for such solutions are sols or colloids. A summary overview may be found in G. Schmid, Cluster and Colloids, From Theory to Applications, VCH Weinheim 1994.

Stable sols are produced by reduction of metal salt solutions with a reducing agent in the presence of a stabilizer which envelops the nanosize particles and prevents further agglomeration of the nanosize particles.

With a suitable choice of reducing agent and stabilizer, it is possible to produce monomodal sols having a narrow particle size distribution. The resulting particle sizes are in the region of <200 nm.

The sol impregnation technique for applying the sols from aqueous solution to supports is likewise known.

Thus, for example, DE-A 195 00 366 describes the production of Pd coated catalysts for hydrogenations by applying the Pd as a highly dilute sol to a support by impregnation or by spraying on, with a shell thickness of less than 5 $\mu$m resulting.

This low shell thickness is not critical for many hydrogenation reactions, but can be a problem in other reactions, e.g. the synthesis of VAM, since the very low noble metal content leads to a reduction in activity. Here, shells in the range 5–1000 $\mu$m, which can accommodate a sufficiently large amount of noble metal, would be desirable. The Pd content of VAM catalysts is in the region of 1% by weight and is thus very high compared to hydrogenation catalysts (0.05–0.5% by weight).

In "Catalyst Preparation Science IV" (Eds.: Delmon, Grange, Jacobs, Poncelet), Elsevier Science Publishers, New York, 1987, pp. 669–687, Michel and Schwartz describe the preparation of bimetallic monodisperse, nanosize Pd—Au particles having 3 different microstructures (alloy, Au shell on a Pd core and vice versa) and their application to a carbon support by adsorption from the colloidal solution.

Schmid, West, Malm, Bovin, Grenthe (Chem. Eur. J., 1996, 2, No. 9, 1099) produce Pd/Au catalysts for the hydrogenation of hexyne by dip coating a $TiO_2$ support in colloidal Pd/Au solutions.

DE-A 44 43 705 describes the preparation of surfactant-stabilized monometal and bimetal colloids from isolable precursors which are soluble in water to a high concentration; these are subsequently used for adsorptive application to catalyst supports from aqueous solution.

DE-A 44 43 701 describes coated catalysts which are obtained by coating the supports with the catalytically active metals in aqueous solutions of monometallic or bimetallic colloids of these metals, with the colloids being stabilized by strongly hydrophilic surfactants.

The sol impregnation technology is thus based on a two-step procedure, namely the preparation of the sols by means of a reduction step and, if appropriate after further isolation and purification steps, subsequent fixing to a support. This process consisting of a plurality of steps is relatively complicated per se.

It is therefore an object of the present invention to provide a simple process for producing a catalyst comprising one or more metals selected from the group consisting of metals encompassing transition groups Ib and VIIIb of the Periodic Table of the Elements on porous support particles.

A further object of the invention is to provide a process for producing sol-coated supported catalysts which can be carried out without great expense.

Another object of the invention is to provide an improved process for producing coated catalysts on porous, preferably nanoporous, supports, in which the resulting shell thicknesses are sufficient for the preparation of vinyl acetate (VAM synthesis).

A further object of the invention is to produce an active and selective, coated VAM catalyst based on Pd/Au quickly and inexpensively in a small number of process steps while at the same time enabling the shell thickness to be controlled readily.

These objects and also further objects which are not listed in more detail but can be derived or deduced from the introductory discussion of the prior art are achieved by a process of the type mentioned at the outset and having the features of claim 1. Advantageous modifications of the process of the invention are claimed in the subordinate claims dependent on claim 1.

A process for producing a catalyst comprising one or more metals selected from the group consisting of metals encompassing transition groups Ib and VIIIb of the Periodic Table of the Elements on porous support particles, which comprises, in a first step, applying one or more precursor(s) selected from the group of compounds consisting of the compounds of metals of transition groups Ib and VIIIb of the Periodic Table to a porous support; and, in a second step, treating the porous support to which at least one precursor has been applied with at least one reducing agent to give nanosize metal particles produced in situ in the pores of the support;

provides, in a particularly advantageous manner, a process which improves the known processes both in respect of the simplicity of carrying out the process and in terms of universal applicability as well as the quality of the resulting process products in a way which could not readily have been foreseen.

In carrying out the process of the invention, a series of advantages compared to the known methods are found:

Thus, in place of the complicated sol impregnation technique (comprising the steps: sol preparation, loading of the support, fixing), use is made of a very simple process comprising fewer steps in which the sol is prepared in situ in the pores of the support by reduction. Here, the preparation of the sol and its fixing to the support are achieved simultaneously in a "single-vessel reaction" having fewer steps or stages than is the case in the processes known from the prior art.

The subsequent reduction step, in particular, which is conventionally required becomes unnecessary in the process of the invention, since the formation of the shell structure and the reduction to the metals occur simultaneously in one step.

The technique according to the invention makes it possible to obtain, in a simple manner, coated catalysts whose shell thickness can be matched to requirements more readily than is the case for known techniques.

In particular, greater shell thicknesses are, if desired, also possible than when using the conventional sol impregnation technique in which the diffusion of the sols from the outside into the pores of the support is also hindered by the mechanical sieve effect.

Shell-like loading with metal salts in the preimpregnation by known techniques and rapid removal of water during drying, e.g. under reduced pressure, in addition to the reduction method of the invention promote the formation of shells or allow a further reduction in the shell thickness, if this is desired.

Furthermore, the process of the invention makes possible higher noble metal loadings on the support, saves process steps and the energy-intensive treatment with highly dilute solutions is avoided.

The invention makes it possible to obtain catalyst particles of significantly better uniformity, a narrower, essentially monomodal particle size distribution and smaller particle sizes compared to conventional preparation techniques.

It is very advantageously possible, in the case of a well-defined pore structure of the support, to set the colloid size exactly via the pore size of the support, so that monomodal distributions of colloids can be produced more simply.

In the known techniques, impurities in sols lead to larger particle sizes and to agglomeration of particles. In contrast, the meticulously clean apparatus and solvents (twice-distilled water) required for the preparation of sols become completely unnecessary in the procedure employed according to the invention, i.e. in-situ preparation.

In the case of VAM catalysts, the invention has the advantage of a tremendous time saving (and thus cost saving) in the production procedure compared to industrial processes involving precipitation of noble metal hydroxides using NaOH followed by a reduction step, since according to the invention the shell can be produced in a few minutes while the NaOH precipitation extends over more than 20 hours.

Owing to the small particle size possible, the uniformity of the particle size distribution and the great shell thickness possible, coated catalysts obtainable by the process of the invention display high activities and selectivities and have good long-term stability.

In the present invention, the pores in a surface zone of the support system are utilized as "microreactors" for the in-situ synthesis of stabilized or unstabilized colloids which are, after final drying, fixed as finely divided nanosize particles to the support.

Support materials which can be used in the process of the invention are therefore all porous materials which have a suitable porosity, i.e. are microporous, nanoporous or mesoporous, and are essentially inert for the purposes of the intended use and the production process. The support materials can have any shape and the shape can be matched to the use.

In an advantageous embodiment of the process of the invention, use is made of an inert, porous, preferably nanoporous, support comprising silicon dioxide, aluminum oxide, titanium dioxide, zirconium dioxide, oxide mixtures of the compounds-mentioned, mixed oxides of the compounds mentioned and/or aluminum silicates in the form of powders, sheets, strips, membranes, rods, plates, tablets, wagon wheels, monoliths, spheres, chips, rings, solid extrudates, hollow extrudates, stars or other shaped bodies.

It is particularly advantageous to employ $SiO_2$, $Al_2O_3$, mixed oxides of $SiO_2$ and $Al_2O_3$ or mixtures of these oxides in the form of spheres, tablets, rings, stars or other shaped bodies as supports.

The diameter or the length and thickness of the support particles is generally from 3 to 9 mm. The surface area of the support, measured by the BET method, is generally 10–500 $m^2/g$, preferably 20–250 $m^2/g$. The pore volume is generally from 0.3 to 1.2 ml/g.

Of particular interest are porous, preferably nanoporous, aluminum oxide supports, for example in the form of membranes, tablets, spheres or powders.

The nanoporous support materials described here as preferred are known per se, as are the microporous or mesoporous supports.

Thus, for example, nanoporous aluminum oxide support membranes are commercially available: they have regularly arranged nanopores having a pore width in the range from about 1 to 500 nm and a depth of up to 500 $\mu$m. The pore density is usually in the range from $10^9$ to $10^{12}$ pores/$cm^2$.

Reviews describing the structure, production and properties of porous anodic oxide films are given by J. W. Diggle et al., Chem. Rev. 69, 365–405 (1969) and J. P. Gullivan et al., Proceeding of the Royal Society of London, 317 (1970), 51 ff.; further information may be found in C. A. Foss et al. J. Phys. Chem. (1994), 98, 2963–2971 and C. K. Preston et al., J. Phys. Chem. (1993), 97, 8495–8503.

The nanoporous structures can be generated in principle and preferably by anodic oxidation of metal surfaces, preferably aluminum surfaces, in an aqueous solution comprising a diprotic or triprotic acid.

Acids which are suitable for this purpose are, in particular, sulfuric acid, oxalic acid, phosphoric acid and chromic acid. The anodic oxidation of aluminum to produce the membranes to be used according to the invention is usually carried out at a low temperature, for instance from 0 to 5° C., and preferably using sulfuric acid or oxalic acid as electrolyte because this allows thick and hard porous films to be obtained. In the production of the films, for example, a sheet of highly pure aluminum forms the anode in an electrochemical cell. Anodization is carried out with precise control of potential and current. The pore diameter is dependent on the electrolyte, the temperature and the anodization voltage, with the diameter increasing with increasing voltage: a guideline in the case of sulfuric acid as electrolyte is 1.2 nm of pore width per volt of applied potential. Use of oxalic acid allows thicker films to be produced than when using sulfuric acid. After the anodic oxidation, unoxidized aluminum on the barrier side can, in a known manner, be dissolved off in an acid bath or be ground off (see, for example, U.S. Pat. No. 4,687,551), giving nanoporous $Al_2O_3$ membranes having one closed surface (barrier side) and one open (=pore openings) surface. Grinding down the membranes into the bottom region of the pores gives first membranes having one open side and one half-open (=very small pore openings)

side; further grinding down makes it possible to obtain membranes having pore openings of about equal width which go through from one side to the other. Alternatively, through pores can also be obtained by etching with, for example, KOH in glycol, with the membrane being placed on the etching bath with the barrier side in contact with the bath.

In the process of the invention, inter alia, one or more precursor(s) selected from the group of compounds consisting of the compounds of metals of transition groups Ib and VIIIb of the Periodic Table is applied to a porous support.

This application or loading can be carried out in many ways which are known per se to those skilled in the art, as long as immobilization of the metal compound(s) in the form of the metal or of alloys on the support is possible. Thus, for example, deposition from the gas phase by CVD techniques known per se is possible.

A preferred process modification provides for the noble metal compound(s) to be applied to the porous support by steeping, spraying, dipping, impregnation, spray drying, hi-coating or fluidized-bed coating, preferably by impregnation.

The loading of the support with the noble metal compound(s) can be carried out in one or more sequential steps, with, if desired, drying phases being able to be inserted between individual fixing steps.

As active metals which can be concentrated on the support, if desired in a shell, all reducible metals from transition groups Ib and VIIIb of the Periodic Table, in particular all noble metals in these groups, inclusive of their mixtures, are suitable.

In a preferred modification of the process of the invention, one or more compound(s) of metals selected from the group consisting of copper, silver, gold, iron, cobalt, nickel, ruthenium, rhodium, osmium, iridium, palladium and platinum is/are applied to the support.

Among these, compounds of Pd, Au, Pt, Ag, Rh, Ru, Cu, Ir, Ni and/or Co are preferred. Particular preference is given to compounds of Pd, Au, Pt, Ag and/or Rh.

In a further advantageous variant of the process of the invention, one or more palladium compound(s) alone or one or more palladium compound(s) together with one or more compound(s) of metals selected from the group consisting of copper, silver, gold, iron, cobalt, nickel, ruthenium, rhodium, osmium, iridium and platinum is/are applied to the support.

An extremely advantageous variant comprises applying one or more palladium compound(s) together with one or more compound(s) of gold to the support.

An essential measure in the process of the invention is treating the porous support to which at least one precursor (precursor compound of the active metal) has been applied with at least one reducing agent to give nanosize metal particles and/or alloy particles produced in situ in the pores of the support.

Suitable reducing agents are all compounds which are capable of reducing the metal compounds used, preferably salts, particularly preferably Pd and Au salts, to the metals.

In a particular embodiment of the process, use is made of one or more reducing agents selected from the group consisting of citrates such as potassium citrate, sodium citrate, ammonium citrate; hydrazine, hydroxylamine, sodium hypophosphite, alkali metal borohydrides such as sodium borohydride, potassium borohydride; gaseous reducing agents such as hydrogen, carbon monoxide; formaldehyde, formates, acetates, oxalates, suitable sulfanilates such as sodium hydroxymethanesulfinate; and monohydric or dihydric alcohols such as ethanol, ethylene glycol.

Among these, preference is given to (alkali metal/alkaline earth metal/ammonium) citrates, formates, acetates, alkali metal borohydrides, oxalates and suitable sulfanilates.

An advantageous embodiment of the invention uses ammonium citrate, potassium citrate and/or sodium citrate as reducing agent.

Particular preference is given to potassium citrate.

The reducing agent is generally used in a stoichiometric amount based on the metal compound(s), but is preferably used in a small excess. The excess can be, for example, from 1.1 to 2, preferably from 1.1 to 1.5, mole equivalents.

In the process of the invention, the in-situ reduction is preferably carried out at temperatures from room temperature to 150° C.

In a particularly advantageous embodiment of the invention, a solution of the metal compound(s) is applied to the porous supports; for example, the support are impregnated by steeping in or dipping into a solution. This solution can basically be solution of the metal compound(s) in an aqueous or organic solvent. Thus, it is possible to apply an aqueous solution, a solution in an organic solvent or a mixture thereof to the support.

As solvents, it is possible to use all compounds in which the salts selected are soluble and which can easily be removed again by drying after the impregnation.

Particular preference is given to using water as solvent. Here, the nature and purity of the water is of only subordinate importance. It is possible to use deionized water, distilled water or twice-distilled water. Likewise, mains water can also be used as long as the materials present therein do not have an adverse effect on the process of the invention for producing the catalysts.

The nature of organic solvents can vary depending on the nature of the metal compound(s) to be dissolved.

For example, unsubstituted carboxylic acids, in particular acetic acid, are especially suitable for salts such as acetates. Water is especially suitable for chlorides.

The additional use of a further solvent is advantageous when the salts are not sufficiently soluble in acetic acid or in water. As additional solvents, it is possible to use those which are inert and are miscible with acetic acid or water. Examples of additives to acetic acid are ketones such as acetone and acetylacetone, also ethers such as tetrahydrofuran or dioxane, acetonitrile, dimethylformamide as well as hydrocarbons such as benzene.

Good results can also be obtained using, as organic solvent, methanol, ethanol, ethylene glycol, N-methylpyrrolidone, dimethylformamide, dimethylacetamide and/or tetrahydrofuran or a mixture of these substances with water.

The compounds of the noble metals serve as precursor, i.e. a compound of the metals which can be converted to the metal by reduction. These can be ionic and nonionic compounds.

Salts are by far the most preferred metal compounds to be used as precursors.

Suitable salts are all salts of the metals which are soluble and contain no constituents which can poison the catalyst, e.g. sulfur. Preference is given to the acetates and the chlorides.

If palladium precursor compounds are used, preference is given to soluble palladium compounds, in particular water-soluble salts selected from the group consisting of palladium (II) acetate, palladium(II) chloride, palladium(II) nitrate and sodium tetrachloropalladate(II) [$Na_2PdCl_4$].

In the case of the chlorides, $PdCl_2$ and $Na_2PdCl_4$ are particularly preferred precursors.

Further soluble metal compounds which are preferably used, in particular water-soluble salts, are tetrachloroauric (III) acid [HAuCl$_4$], gold(III) acetate [Au(OAc)$_3$], potassium aurate [KAuO$_2$], hexachloroplatinic(IV) acid hydrate, hexachloroiridic(IV) acid hydrate, ruthenium(III) chloride, ruthenium(III) nitrate and/or rhodium(III) chloride hydrate.

In the case of the chlorides, it generally has to be ensured that the chloride ions are removed from the catalyst before use. This is achieved by washing the doped support, e.g. with water, after the metals have been fixed to the support by reduction to the nanosize metallic particles.

The metal compounds are usually used in concentrations of from about 0.1 to 100 g per liter, preferably from 1 to 50 g per liter, based on the solvent.

Although stable catalysts comprising nanosize particles on a support are obtainable without further additives, the application of the precursor(s) to the porous, preferably nanoporous, support and/or the reduction of the support to which the precursor(s) has/have been applied in the process of the invention are/is preferably carried out in the presence of a colloid stabilizer or a plurality of colloid stabilizers.

Suitable stabilizers are all compounds which are able to complex the nanosize particles obtained by reduction by enveloping them and are thus capable of preventing further growth and the agglomeration of the nanosize particles.

Stabilizers which can be used for the purposes of the invention include, inter alia, betaines, surfactants, polymers such as polyvinylpyrrolidone (PVP), polyvinyl alcohol (PVA), polyacrylamide (PAA), polyelectrolytes, citrates, substituted phosphines, substituted sulfanilic acids, chlorides, amino acids or mixtures thereof. It is also possible, inter alia, to use copolymers which are built up of monomers containing betaine groups plus further monomers such as acrylic acid, acrylic esters, acrylamides, vinyl carboxylates, vinyl alkyl ethers, N-vinylpyridine, N-vinylpyrrolidone or N-vinylcarboxamides.

In a favorable embodiment of the process, one or more compound(s) selected from the group consisting of betaines, PVP, phosphines, citrates, oxalates, formates, acetates, sulfanilates, PVA and PAA is/are added as colloid stabilizer.

Preference is given to betaines, PVP, PVA, citrates, substituted phosphines, substituted sulfanilic acids and/or chlorides.

Particular preference is given to potassium citrate, ammonium citrate, PVP K 30, dimethyldodecylammonium propane sulfonate.

In the process of the invention, the stabilizers are usually used in an amount of from 5 to 1000% by weight, based on the metal or metals.

The addition of the stabilizer can take place in any order. The stabilizer can be added to the metal compound with which the support is impregnated. The support can first be impregnated with the colloid stabilizer. The impregnated support can be brought into contact with the colloid stabilizer. The colloid stabilizer or stabilizers can also be employed together with the reducing agent. Subsequent stabilization (after reduction) is also possible under some circumstances.

In a very particular variant of the invention, use is made of one or more compounds which simultaneously act as colloid stabilizer and as reducing agent. This means that reducing agent and stabilizer can also be identical. Thus, for example, potassium citrate acts both as reducing agent and as stabilizer in the case of Pd/Au.

Preference is therefore given, according to the invention, to using ammonium, potassium and/or sodium citrate as reducing agent and colloid stabilizer.

Potassium citrate is especially advantageous.

The stabilizer can remain on the nanosize particles after they have been fixed on the support or may be removed if the presence of the stabilizer should interfere with the catalytic function. The complete or partial removal of the stabilizer can, if required, be carried out, for example, hydrolytically using a solvent, thermally or oxidatively, e.g. by burning off in air at from 300 to 500° C., either before installation of the catalyst in the reactor or else in situ in the reactor.

The application of metal compound(s) and their reduction to the support can be carried out successively in two steps or in a "single-vessel reaction".

In one variant, it can be preferred for the first and second steps to be carried out successively. This advantageously allows the porous, preferably nanoporous, support to which at least one metal compound has been applied to be subjected to a drying step prior to the reduction. This allows, for example, various "shells" of metal compounds to be applied to the support by multiple repetition of impregnation and drying.

Alternatively, it is also preferred for the first and second steps to be carried out in a single-vessel process without isolation, purification or drying of the porous, preferably nanoporous, support to which the precursor(s) has/have been applied.

In a preferred embodiment of the invention, a support is first preimpregnated with essentially aqueous salt solutions of reducible active metals, which preimpregnation does not have to lead to a shell, i.e. the support is, under some circumstances, "fully impregnated".

However, a shell and thus a coated catalyst can also be produced. This is achieved, for example, by specific incomplete impregnation of the support and/or by carrying out the reduction in an appropriate manner.

Impregnation and subsequent, if desired after a drying step, treatment with a reducing agent under such conditions (concentration, temperature, time, etc.) and in the presence or absence of stabilizers results in the active metals being reduced to the metals in the oxidation state 0, so that they can be concentrated as nanosize particles in a shell of the support body to produce a catalyst of the egg shell or egg white type.

Thus, the application of the precursor(s) and/or the reduction are/is preferably carried out so that the metal compounds are reduced in the pores of the support in a shell-like surface zone to generate the corresponding metals or alloys in the form of stabilized or unstabilized nanosize particles so as to give a coated catalyst.

Gaseous reducing agents such as H$_2$ or CO or ethylene can only be used when a shell structure has already been produced on impregnation with the metal salts.

As regards the mechanism of shell formation in the production of noble metal coated catalysts on porous, shaped ceramic supports, it may be assumed, without thereby restricting the invention to a mechanism, that rapid reduction takes place at the internal interface between active metal salt and reducing agent to give the nanosize particles, the particles are immobilized in the outer shell because of their size (including the envelope of stabilizer) and further active metal salt diffuses from the inner regions of the shaped body toward the surface so that it is likewise reduced within the shell after reaching the slowly inward-moving reducing agent front and is deposited on the support.

A significant advantage of the invention is, inter alia, that particularly stable shells of relatively great thickness can be produced. A shell thickness in the range from 5 $\mu$m to 5000 $\mu$m is preferably obtained.

Coated catalysts which have nanosize particles having a mean particle diameter in the range from 1 to 100 nm in the pores and in the shell are advantageously obtained. This means that the particles of the shell do not agglomerate or agglomerate only a little.

The support can, before, during and/or after the in-situ generation of the nanosize particles, be loaded with further activators, in particular alkali metal acetates, and, if desired, promoters, for example Zr, Ti, Cd, Cu, Ba and/or Re compounds.

A particularly interesting modification of the process therefore includes application of one or more activators and/or promoters after, before or during the application of the precursor(s) and/or the reduction.

Some preferred catalyst systems which can be produced according to the invention, preferably coated catalysts, comprise, for example, not only palladium and gold but also potassium acetate as activator and/or cadmium or barium compounds as promoters.

The metal contents of particularly preferred catalysts are as follows:

The Pd content of the Pd/K/Cd and the Pd/K/Ba catalysts is generally from 0.6 to 3.5% by weight, preferably from 0.8 to 3.0% by weight, in particular from 1.0 to 2.5% by weight.

The Pd content of the Pd/Au/K catalysts is generally from 0.5 to 2.0% by weight, preferably from 0.6 to 1.5% by weight.

The K content of all three types of catalyst is generally from 0.5 to 4.0% by weight, preferably from 1.5 to 3.0% by weight.

The Cd content of the Pd/K/Cd catalysts is generally from 0.1 to 2.5% by weight, preferably from 0.4 to 2.0% by weight.

The Ba content of the Pd/K/Ba catalysts is generally from 0.1 to 2.0% by weight, preferably from 0.2 to 1.0% by weight.

The Au content of the Pd/K/Au catalysts is generally from 0.2 to 1.0% by weight, preferably from 0.3 to 0.8% by weight.

At least one salt of each of the elements to be applied to the support particles (for example Pd/K/Au, Pd/K/Cd, Pd/K/Ba) has to be applied. It is possible to apply a plurality of salts of one element, but it is usual to apply exactly one salt of each of the three elements. The necessary amounts of the salts can be applied in one step or by multiple impregnation. The salts can be applied to the support by known methods such as steeping, spraying on, vapor deposition, dipping or precipitation.

In the method of the invention, it is naturally only the noble metal salts, i.e. Pd and Au, which are reduced to the corresponding nanosize noble metal particles and not the "base" constituents K, Cd, Ba. The latter can be applied to the support together with the noble metal salts or else beforehand or afterwards.

Normally, according to the method of the invention, a shell of Pd/Au is first produced and the support is then further impregnated with potassium acetate solution, with the K being distributed uniformly over the cross section of the pellet.

If a plurality of noble metals are to be fixed to the support (e.g. Pd and Au), alloys or structured nanostructures, i.e. gold on palladium or palladium on gold, can also be produced by the method of the invention.

The coated catalysts produced by the process of the invention can be used for many heterogeneously catalyzed reactions.

These include, inter alia, aminations, hydrogenations, dehydrogenations, dehydrocyclizations, hydroxylations, oxidations, epoxidations, skeletal isomerizations and also combinations of these types of reaction for the targeted conversion of organic molecules.

The impregnated and reduced shaped bodies can be used, in particular after activation, as coated catalysts for hydrogenation, oxidation and isomerization reactions, particularly preferably for selective hydrogenation reactions and partial oxidations.

Examples of these include: selective hydrogenation of propyne, selective hydrogenation of butadiene, selective hydrogenation of acetylene, selective hydrogenation of butynol, selective hydrogenation of octadiene to octene, selective hydrogenation of benzene to cyclohexene, hydrogenation of carbon monoxide, hydrogenation of carbon dioxide, hydrogenation of maleic anhydride, hydrogenation of $NO_x$ to $NH_3$ or $NH_2OH$, carboxamides from nitrites, amines from carboxylic acids, amination of aromatics, in particular the reaction of benzene with ammonia to give aniline, reductive amination of aldehydes and ketones to amines, the Wacker synthesis, acetaldehyde from ethylene, oxidation of butane to maleic anhydride, oxidation of carbon monoxide, oxidation of alcohols to aldehydes, ketones or carboxylic acids, oxidations of alkanes to alcohols, aldehydes and ketones, oxidations of aldehydes and ketones to carboxylic acids, hydroxylation of aromatics, e.g. oxidation of benzene to phenol or toluene to cresol, oxidation of propylene to acrolein or acrylic acid, ammonoxidation of, for example, toluene to benzonitrile or of propylene to acrylonitrile, epoxides can be converted into aldehydes/ketones and under hydrogenating conditions into alcohols, e.g. styrene oxide derivatives to give the corresponding phenylacetaldehydes or under hydrogenating conditions to phenylethanols.

Pd/Au coated catalysts produced according to the invention can be advantageously used in the vinyl acetate synthesis to prepare vinyl acetate in the gas phase from ethylene, acetic acid and oxygen or oxygen-containing gases.

The preparation of vinyl acetate is generally carried out by passing acetic acid, ethylene and oxygen or oxygen-containing gases at temperatures of from 100 to 220° C., preferably from 120 to 200° C., and pressures of from 1 to 25 bar, preferably from 1 to 20 bar, over the finished catalyst, with unreacted components being able to be circulated. The oxygen concentration is advantageously kept below 10% by volume (based on the gas mixture without acetic acid). However, under some circumstances, dilation with inert gases such as nitrogen or carbon dioxide is advantageous. Carbon dioxide is particularly suitable for dilution since it is formed in small amounts during the reaction.

In the synthesis of vinyl acetate (VAM), it has been found that the supported catalysts used for the synthesis from ethylene, acetic acid and oxygen preferably comprise Pd and an alkali metal, preferably K. As further additives, Cd, Au or Ba are successfully used.

The metal salts can be applied to the support by steeping, spraying on, vapor deposition, dipping or precipitation.

In the case of Pd/Au/K catalysts, it has been found to be advantageous to apply the two noble metals in the form of a shell on the support, i.e. the noble metals are present only in a zone close to the surface while the regions further inside the support body are virtually free of noble metals. The thickness of these catalytically active shells is about 0.1–2 mm.

The process can be carried out more selectively using coated catalysts than when using catalysts in which the support particles are impregnated right into the core ("fully impregnated"), or the capacity can be increased.

In the latter case, it is possible to keep the reaction conditions unchanged compared to the fully impregnated catalysts and to produce more vinyl acetate per reactor volume and unit time. This makes the work-up of the crude vinyl acetate obtained easier, since the vinyl acetate content in the gas leaving the reactor is higher, which also leads to an energy saving in the work-up section. Suitable work-ups are described, for example, in U.S. Pat. No. 5,066,365, DE 34 22 575, DE 34 08 239, DE 29 45 913, DE 26 10 624, U.S. Pat. No. 3,840,590. If, on the other hand, the plant capacity is kept constant, the reaction temperature can be lowered and as a result the reaction can be carried out more selectively at the same total throughput, thus saving starting materials. In this case, the amount of carbon dioxide which is formed as by-product and therefore has to be removed as well as the loss of entrained ethylene associated with this removal are also reduced. Furthermore, this procedure leads to a lengthening of the operating life of the catalyst.

For this reaction, the invention provides a single-stage process for producing sol-coated supported catalysts by generating the sols in situ in the pores of the support by reduction, i.e. preparation of the sol and fixing to the support are carried out simultaneously in one step. In this way, the shell thickness can be more readily matched to requirements, in particular greater shell thicknesses are possible than is the case with the sol impregnation technique in which the diffusion of the sol from outside into the pores of the support is also hindered by the mechanical sieve effect. Furthermore, higher noble metal loadings on the support are possible, process steps are saved and the energy-intensive treatment with highly dilute solutions is avoided. If desired, in the case of well-defined pore structures in the support, the colloid size can be set exactly via the pore size of the support, so that monomodal distributions of colloids can be obtained more simply. The meticulously clean apparatus and solvents (twice-distilled water) required for the preparation of sols become completely unnecessary in the in-situ preparation. Impurities in sols lead to larger particle sizes and to agglomeration of particles.

Shell-like loading with metal salts in the preimpregnation by means of known techniques and rapid removal of water during drying, e.g. under reduced pressure, in addition to the reduction method of the invention promote the formation of shells or allow a further reduction in the shell thickness, if this is desired.

The catalysts obtained according to the invention have a significantly more uniform active metal distribution and higher noble metal dispersion than do VAM catalysts produced in a conventional manner. The high dispersion is also largely maintained in long-term operation owing to the reduced agglomeration of the noble metal particles, as a result of which the deactivation of the catalysts obtained according to the invention is slowed and long operating lives are obtained. The production process of the invention advantageously leads to an essentially monomodal and very narrow particle size distribution.

Furthermore, the mean noble metal particle diameters are significantly smaller than in the case of conventional catalysts. This results in a high active metal surface area and thus a high catalytic activity.

The following examples serve to explain and illustrate the invention without it being restricted to these.

EXAMPLE 1

200 g of $SiO_2$ supports (Siliperl AF125, Engelhard) having a BET surface area of 300 m$^2$/g were sprayed discontinuously at a temperature of 30–32° C. with a hydrochloric acid solution of 3.33 g (18.8 mmol) of palladium chloride and 1.85 g (4.7 mmol) of auric acid in 500 ml of water over a period of 35 minutes in a coating unit. The support spheres were subsequently dried and sprayed with 20 g of tripotassium citrate hydrate dissolved in 200 ml of water over a period of 25 minutes. At a drum rotation speed of 10 rpm, spraying was carried out discontinuously at 1 bar. The inlet temperature (warm air temperature) was 60° C. and the product temperature was 32–30° C. This gave a homogeneously impregnated coated catalyst having a shell thickness of 400 µm.

The diameter of the nanosize particles was determined by means of TEM. The mean particle diameter is 30 nm.

EXAMPLE 2

20 g of the same support as in Example 1 were impregnated with a solution of 335 mg of palladium chloride and 186 mg of auric acid by steeping and dried. At 65° C., the support was impregnated with 1.52 g of trisodium citrate dihydrate in 19.6 ml of water and, after being left to stand for three hours at 65° C., was dried.

After cutting through a representative number of pellets, the shell thickness was measured by means of optical microscopy and XPS line scans. The shell thickness is 1 mm.

The diameter of the nanosize particles was determined by means of TEM. The mean particle diameter is 40 nm.

EXAMPLE 3

20 g of $SiO_2$ supports (Aerosil 200, Degussa) were impregnated with a solution (19.6 ml) of 325 mg (1.89 mmol) of palladium chloride and 189 mg (0.473 mmol) of auric acid by steeping and dried. The supports were wetted with 19 ml of water by steeping and impregnated with 1.68 g of tripotassium citrate in 10 ml of water and dried.

After cutting through a representative number of pallets, the shell thickness was measured by means of SEM.

The shell thickness is 140 µm.

The diameter of the nanosize particles was determined by means of TEM. The mean particle size is 60 nm.

EXAMPLE 4

Palladium chloride (335 mg) and auric acid (186 mg) were dissolved in water (19.6 ml) and applied by steeping to Siliperl AF 125 $SiO_2$ supports (10.0 g). The supports were dried and impregnated with an aqueous solution of potassium formate (0.5 g) and sodium sulfanilate (0.2 g) and dried again. The Pd/Au ratio is Pd:Au=8:2.

EXAMPLE 5

186 mg of auric acid were applied to Siliperl AF 125 by steeping, the supports were dried at 120° C. and reduced by means of citrate solution (19.6 ml). After 12 hours, the dark gray beads were dried and subsequently impregnated with 16 ml of an acetic acid solution of palladium acetate (424 mg, 1.89 mmol) at 60° C. Drying was carried out in a vacuum drying oven where the Pd salt was thermally reduced at 120° C.

The particle diameter of the nanosize particles was determined by means of TEM. The mean diameter is 20 nm.

EXAMPLE 6

325 mg of palladium chloride and 186 mg of auric acid were dissolved in water. 20 g of supports (Siliperl AF 125) were placed in a round-bottom flask (250 ml) and impregnated with auric acid and palladium chloride solution (19.6 ml). The supports were subsequently dried for 4 hours at 120° C. It was impregnated with a viscous potassium citrate solution (10 ml), shaken well and dried again.

The shell has a thickness of 75 μm and is black.

EXAMPLE 7

Auric acid (189 mg, 0.473 mmol) and palladium chloride (325 mg, 1.89 mmol) were dissolved in water. The $SiO_2$ support (20.0 g; type D11-10, BASF) was impregnated with the solution and subsequently dried for 5 hours at 120° C. After cooling, water (A=16 ml, D=19 ml) was added to the various supports in order to finally allow a tripotassium citrate solution (1.68 g in 10 ml) to diffuse in. During the addition of water, the color of the support changed from beige to white. The support was dried for 5 hours at 120° C.

Reactor Tests:

The catalysts produced in the examples and comparative examples are tested in a fixed-bed tubular microreactor having a capacity of 36 ml. The gases are metered in via MFCs, the acetic acid is metered in using an LFC (Bronkhorst). The gases and the acetic acid are mixed in a gas mixing tube charged with packing elements. The output from the reactor is let down to atmospheric pressure and passed through a glass condenser. The condensate collected is analyzed off-line using GC. The uncondensable gases are determined quantitatively by on-line GC.

Before the measurement, the catalyst is activated in the reactor as follows:

The catalyst is heated from about 25° C. to 155° C. under $N_2$ at atmospheric pressure.

At the same time, the gas temperature is increased to 150° C. and the gas mixing temperature is increased to 160° C. The conditions are maintained for some time.

Subsequently, ethylene is fed in and the pressure is increased to 10 bar. After a hold time, acetic acid is metered in and the conditions are maintained for some time.

After activation, the catalyst is run up and measured as follows:

Oxygen is added downstream of the gas mixing tube and the oxygen concentration is increased stepwise to 4.8% by volume ($1^{st}$ measurement) and later to 5.2% by volume ($2^{nd}$ measurement). Care always has to be taken to ensure that the explosion limits of the ignitable ethylene/$O_2$ mixture are not exceeded. At the same time, the reactor temperature is increased to 170° C.

The reaction is monitored continually using the gas chromatograph.

When the reaction is proceeding in a steady state, i.e. with a constant reactor temperature and constant concentrations of vinyl acetate and $CO_2$ in the product gas stream, sampling is commenced.

Over a period of about 1 hour, one liquid sample and a number of gas samples are taken.

The product gas flow is determined using a gas meter. After testing is complete, the oxygen concentration is first decreased stepwise.

The compositions of the catalysts used are shown in Table 1. The reactor results obtained are shown in Table 2.

TABLE 1

Catalyst data

| Ex./Comp. | Precursors | Reducing agent | Stabilizer | Shell thickness [μm] |
|---|---|---|---|---|
| 2 | $PdCl_2$, $HAuCl_4$ | Sodium citrate | — | 1000 |
| 3 | $PdCl_2$, $HAuCl_4$ | Potassium citrate | — | 140 |
| 4 | $PdCl_2$, $HAuCl_4$ | Potassium formate | Sodium sulfanilate | 250 |
| 5 | $HAuCl_4$, $Pd(OAc)_2$ | Potassium citrate | — | 200 |
| 6 | $PdCl_2$, $HAuCl_4$ | Potassium citrate (viscous) | — | 75 |
| 7 | $PdCl_2$, $HAuCl_4$ | Potassium citrate | — | 150 |

TABLE 2

Catalyst performance in the microreactor

| Ex./Comp. | Composition | Support | $O_2$ feed conc. [%] | Coating method | Selectivity [%] | STY [g/l*h] |
|---|---|---|---|---|---|---|
| 2 | Pd/Au = 4:1 | Siliper1 | 4.8 | impregnation | 90.3 | 93 |
| 3 | Pd/Au = 4:1 | Aerosil 200 | 4.8 | impregnation | 90.7 | 110 |
| 4 | Pd/Au = 4:1 | Siliper1 | 4.8 | impregnation | 86.3 | 49 |
| 5 | Pd/Au = 4:1 | Siliper1 | 4.8 | impregnation | 92.0 | 147 |
| 6 | Pd/Au = 4:1 | Siliper1 | 4.8 | impregnation | 89.7 | 110 |
| 7 | Pd/Au = 4:1 | D11–10 | 4.8 | impregnation | 88.9 | 70 |

Further advantages and embodiments of the invention can be derived from the following claims.

What is claimed is:

1. A process for producing a catalyst comprising one or more metals selected from the group of metals encompassing transition groups Ib and VIIIb of the Periodic Table of the Elements on porous support particles, which comprises, in a first step, applying one or more precursor(s) selected from the group of compounds consisting of the compounds of metals of transition groups Ib and VIIIb of the Periodic Table to a porous support;

and, in a second step, treating the porous support to which at least one precursor has been applied with at least one reducing agent to give nanosize metal particles produced in situ in the pores of the support.

2. The process as claimed in claim 1, wherein at least one member of the group of an inert, porous, nanoporous support selected from the group consisting of silicone dioxide, aluminum oxide, titanium dioxide, zirconium dioxide, oxide mixtures of the compounds mentioned, mixed oxides of the compounds mentioned and aluminum silicates in the form of powders, sheets, strips, membranes, rods, plates, tablets, wagon wheels, monoliths, spheres, chips, rings, solid extrudates, hollow extrudates, stars or other shaped bodies is used.

3. The process as claimed in claim 1, wherein the metal compounds(s) is/are applied to the porous support by steeping, spraying, dipping, impregnation, spray drying, hi-coating or fluidized-bed.

4. The process as claimed in claim 1, wherein at least one compound of metals selected from the group consisting of copper, silver, gold, iron, cobalt, nickel, ruthenium, rhodium, osmium, iridium, palladium and platinum is applied to the support.

5. The process as claimed in claim 1, wherein at least one palladium compound alone or at least one palladium compound together with at least one compound of metals selected from the group consisting of copper, silver, gold, iron, cobalt, nickel, ruthenium, rhodium, osmium, iridium and platinum, is applied to the porous support.

6. The process as claimed in claim 1, wherein at least one palladium compound together with at least one compound of gold are applied to the porous support.

7. The process as claimed in claim 1, wherein at least one reducing agent selected from the group consisting of potassium citrate, sodium citrate, ammonium citrate; hydrazine, hydroxylamine, sodium hypophosphite, alkali metal borohydrides; gaseous reducing agents; formaldehyde, formates, acetates, oxalates, sulfanilates; and monohydric or dihydric alcohols; are used.

8. The process as claimed in claim 1, wherein the reducing agent used is at least one member selected from the group consisting of potassium citrate, sodium citrate and ammonium citrate.

9. The process as claimed in claim 1, wherein a solution of the metal compound is applied to the porous, nanoporous, support.

10. The process as claimed in claim 9, wherein an aqueous solution, a solution in an organic solvent or a mixture thereof is applied to the support.

11. The process as claimed in claim 10, wherein water is used as solvent.

12. The process as claimed in claim 10, wherein methanol, ethanol, ethylene glycol, N-methyl-pyrrolidone, dimethylformamide, dimethylacetamide and/or tetrahydrofuran or a mixture of one or more of these substances with water is used as organic solvent.

13. The process as claimed in claim 9, wherein water-soluble salts selected from the group consisting of Pd precursors consisting of palladium(II) acetate, palladium(II) chloride, palladium(II) nitrate and sodium tetrachloropalladate(II) [$Na_2PdCl_4$] are used.

14. The process as claimed in claim 9, wherein water-soluble salts, selected from a group consisting of metal precursors consisting of tetrachloroauric(III) acid, gold(III) acetate [$Au(OAc)_3$], potassium aurate [$KAuO_2$], hexachloroplatinic(IV) acid hydrate, hexachloroiridic(IV) acid hydrate, ruthenium(III) chloride, ruthenium(III) nitrate and rhodium(III) chloride hydrate are used.

15. The process as claimed in claim 9, wherein the application of the precursors(s) to the porous, nanoporous, support and/or the reduction of the support to which the precursor(s) has/have been applied are/is carried out in the presence of at least one colloid stabilizer.

16. The process as claimed in claim 15, wherein at least one compound selected from the group consisting of betaines, PVP, citrates, oxalates, formates, acetates, sulfanilates, PVA and PAA is added as colloid stabilizer.

17. The process as claimed in claim 15, wherein use is made of one or more compounds which simultaneously act as colloid stabilizer and as reducing agent.

18. The process as claimed in claim 17, wherein potassium citrate, sodium citrate and/or ammonium citrate is/are used as reducing agent and colloid stabilizer.

19. The process as claimed in claim 1, wherein the first and second steps are carried out successively.

20. The process as claimed in claim 19, wherein the porous, nanoporous, support to which at least one metal compound has been applied is subjected to a drying step prior to the reduction.

21. The process as claimed in claim 1, wherein the first and second steps are carried out in a single-vessel process without isolation, purification or drying of the porous, nanoporous, support to which the precursor(s) has/have been applied.

22. The process as claimed in claim 1, wherein the application of the precursor(s) and/or the reduction are/is carried out in such a way that the metal compounds are reduced in the pores of the support in a shell-like zone close to the surface to give the corresponding metals or alloys in the form of stabilized or unstabilized nanosize particles to produce a coated catalyst.

23. The process as claimed in claim 22, wherein a shell thickness in the range from 5 $\mu$m to 5000 $\mu$m is obtained.

24. The process as claimed in claim 1, wherein catalysts which have metal particles and/or alloy particles which have a mean particle diameter in the range from 1 to 100 nm in the pores and/or the shell are obtained.

25. The process as claimed in claim 1, wherein one or more activators and/or promoters is/are applied after, before or during the application of the precursor(s) and/or the reduction.

26. The process as claimed in claim 1, wherein the in-situ reduction is carried out at temperatures from room temperature to 150° C.

27. In the process for the preparation of vinyl acetate by reacting ethylene, acetic acid and an oxygen gas in the vapor phase in the presence of a catalyst, the improvement comprising using the catalyst produced by the process of claim 22.

\* \* \* \* \*